United States Patent [19]

Gers-Barlag et al.

[11] Patent Number: 5,725,844
[45] Date of Patent: Mar. 10, 1998

[54] WATERPROOF COSMETIC OR DERMATOLOGICAL PHOTOPROTECTIVE PREPARATIONS

[75] Inventors: Heinrich Gers-Barlag, Kummerfeld; Stefan Hachmann, Norderstedt; Bente Nissen; Sabine Schultz, both of Hamburg, all of Germany

[73] Assignee: Beiersdorf AG, Hamburg, Germany

[21] Appl. No.: 495,643

[22] PCT Filed: Jan. 29, 1994

[86] PCT No.: PCT/EP94/00257

§ 371 Date: Nov. 27, 1995

§ 102(e) Date: Nov. 27, 1995

[87] PCT Pub. No.: WO94/17780

PCT Pub. Date: Aug. 18, 1994

[30] Foreign Application Priority Data

Feb. 11, 1993 [DE] Germany .............. 43 03 983.9
Dec. 15, 1993 [DE] Germany .............. 43 42 719.7

[51] Int. Cl.$^6$ .................... A61K 7/42; A61K 7/44
[52] U.S. Cl. .................. 424/59; 424/60; 424/47; 424/400; 424/401; 424/DIG. 5; 514/159; 514/241; 514/245; 514/408; 514/532; 514/679; 514/692
[58] Field of Search .................. 424/59, DIG. 5, 424/47, 60, 400, 401

[56] References Cited

U.S. PATENT DOCUMENTS 5,207,998  5/1993  Robinson et al. .............. 424/59

*Primary Examiner*—Shelley A. Dodson
*Attorney, Agent, or Firm*—Sprung Kramer Schaefer & Briscoe

[57] ABSTRACT

Water-resistant cosmetic or dermatological light protection formulations in the form of O/W emulsions or hydrodispersions, comprising
- one or more cosmetically or pharmaceutically acceptable hydrophobic inorganic pigments, these pigments being incorporated into the oily phase of the emulsions or hydrodispersions,
- one or more cosmetically or pharmaceutically acceptable oil-soluble UV filter substances,
- one or more film-forming agents and furthermore, comprising, if appropriate,
- one or more cosmetically or pharmaceutically acceptable water-soluble UV filter substances
- one or more substances chosen from the group consisting of the customary cosmetic or dermatological active compounds, auxiliaries and/or additives in a customary cosmetic or pharmaceutical carrier.

14 Claims, No Drawings

WATERPROOF COSMETIC OR DERMATOLOGICAL PHOTOPROTECTIVE PREPARATIONS

The present invention relates to water-resistant cosmetic or dermatological light protection formulations, in particular such light protection formulations in the form of emulsions or hydrodispersions.

Cosmetic skin care is primarily to be understood as intensifying or restoring the natural function of skin as a barrier against environmental influences (for example dirt, chemicals, microorganisms) and against the loss of endogenous substances (for example water, natural fats, electrolytes).

If this function is impaired, increased absorption of toxic or allergenic substances or attack by microorganisms and, as a consequence, toxic or allergic skin reactions may occur.

The aim of cosmetic skin care is furthermore to compensate the loss of fats and water from the skin caused by daily washing. This is important especially if the natural regeneration capacity is inadequate. Skin care products furthermore should protect against environmental influences, in particular sun and wind, and delay the signs of ageing of the skin.

Medicinal topical compositions as a rule comprise one or more medicaments in an active concentration. For simplicity, reference is made to the legal regulations of the Federal Republic of Germany (for example cosmetics legislation, Food and Drugs Act) for a clear distinction between cosmetic and medicinal use and corresponding products.

The damaging effect of the ultraviolet part of solar radiation on the skin is generally known. While rays having a wavelength shorter than 290 nm (the so-called UVC range) are absorbed by the ozone layer in the earth's atmosphere, rays in the range between 290 nm and 320 nm, the so-called UVB range, cause erythema, simple sunburn or even burns of greater or lesser severity on the skin.

The narrower range around 308 nm is regarded as a maximum of the erythema activity of sunlight.

Numerous compounds are known for protection against UVB radiation, most of these being derivatives of 3-benzylidenecamphor, of 4-aminobenzoic acid, of cinnamic acid, of salicylic acid, of benzophenone and also of 2-phenylbenzimidazole.

UV filter substances are also important for the wavelength range between about 320 and 400 nm, the so-called UVA range, since such rays can also cause damage. It has thus been proved that UVA radiation leads to damage to the elastic and collagenic fibers of the connective tissue, which makes the skin age prematurely and is to be regarded as a cause of numerous phototoxic and photoallergic reactions. The damaging influence of UVB radiation may be intensified by UVA radiation.

However, UV radiation can also lead to photochemical reactions, the photochemical reaction products then intervening in skin and cell metabolism.

Such photochemical reaction products are chiefly free radical compounds, for example hydroxyl radicals, hydroperoxy radicals and superoxide ions. Undefined free radical photo-products which are formed in the skin itself can display uncontrolled secondary reactions because of their high reactivity. However, even singlet oxygen, an excited state of the oxygen molecule which is not in free radical form, can occur with UV irradiation, as can short-lived epoxides and many others. Singlet oxygen, for example, is distinguished from the triplet oxygen usually present (free radical base state) by an increased reactivity. Nevertheless, excited, reactive (free radical) triplet states of the oxygen molecule also exist.

To prevent these reactions, antioxidants and/or agents which trap the radicals can additionally be incorporated into the cosmetic or dermatological formulations.

Most inorganic pigments which are known to be used in cosmetics to protect the skin from UV rays are UV absorbers or UV reflectors. These are oxides of titanium, zinc, iron, zirconium, silicon, manganese, aluminium, cerium and mixtures thereof, as well as modifications.

Although there are cosmetic and dermatological formulations which are entirely advantageous for protecting the skin against the damaging consequences of the action of UV light, one disadvantage which is often observed is that the formulations are not or not sufficiently water-resistant.

Light protection formulations are required and used particularly frequently on bathing beaches and in open-air swimming pools. It is in this case desirable for the light protection formulation to be largely water-resistant, that is to say for it to be washed off from the skin to only a small extent, if at all.

Higher light protection factors, that is to say, for example, those situated above LF 15, can in general be achieved only by large amounts of UV filter substances. If a sunscreen product is also still to have a high light protection factor after bathing, the UV filter substance in particular must be retained on the skin.

It is in itself already troublesome if the sunscreen product has to be applied again after bathing. During bathing itself, under certain circumstances the use of a light protection formulation which can be washed off is even irresponsible and harmful to the skin, since water absorbs light in the UVA and UVB range poorly, and consequently represents no noticeable UV protection, not even for submerged areas of skin.

For water-resistant light protection formulations, the prior art usually uses UV filter substances which are not water-soluble, water-repellent raw materials (for example silicone oils in high concentrations) and/or film-forming agents, in particular high molecular weight compounds (for example PVP/hexadecene copolymers). Barriers are thereby built up between the UV filter substances lying on the skin and the water.

The disadvantage here is that, although diffusion of the filter substances into the water can be delayed, it cannot be prevented completely. Such products can therefore suffer a considerable loss in protective action during prolonged bathing.

Inorganic pigments are indeed distinguished by a good light protection action. However, they have the disadvantage that it is in general difficult to incorporate them into such formulations in a satisfactory manner.

Another disadvantage of the use of inorganic pigments in cosmetic formulations is that such pigments in by far the most cases lead to severe dryness of the skin.

Since accumulation of the pigment granules to agglomerates must appropriately be prevented, a certain content of emulsifiers or comparable surface- or interface-active substances has always had to be added to the formulations.

Customary cosmetic presentation forms are emulsions, that is to say metastable two- or multiphase systems in which the individual phases are present in the liquid state. O/W emulsions are a familiar type of emulsion.

The use of the customary cosmetic emulsions is in itself acceptable. Nevertheless, emulsifiers, like any chemical substance in the end, can cause allergic reactions or reactions based on hypersensitivity of the user in individual cases.

It is thus known that certain photodermatoses are triggered off by certain emulsifiers, and also by various fats, and simultaneous exposure to sunlight. Such photodermatoses are also called "Majorca ache". An object of the present invention was therefore to develop water-resistant light protection formulations which can also be used as emulsifier-free preparations.

Emulsifier-free light protection preparations based on so-called hydrodispersions have been available to the consumer for some time.

Hydrodispersions are dispersions of a liquid, semi-solid or solid internal (discontinuous) lipid phase in an external aqueous (continuous) phase.

However, in contrast to O/W emulsions, which are distinguished by a similar phase arrangement, hydrodispersions are essentially free from emulsifiers. Hydrodispersions are metastable systems, as furthermore emulsions also are, and tend to pass into a state of two discrete phases which are in themselves coherent. In emulsions, the choice of a suitable emulsifier prevents phase separation.

In the case of hydrodispersions of a liquid lipid phase in an external aqueous phase, the stability of such a system can be ensured, for example, by building up a gel structure in the aqueous phase, in which structure the lipid droplets are suspended in a stable form.

Although this type of formulation offers the advantage of absence of emulsifier compared with the conventional light protection formulations, there are on the other hand also some points which require improvement. For a good light protection action of such preparations, a comparatively high concentration of UV filters is thus necessary. Furthermore, such preparations usually feel tacky, in contrast to emulsions and light protection oils.

A tacky sunscreen product, however, is particularly unpleasant precisely during summertime heat, that is to say the usual temperature at which such formulations are used, especially if particles of sand also get onto the treated skin.

Another object was therefore to provide water-resistant light protection preparations which, if desired, can have a relatively low concentration of UV filters and furthermore impart a pleasant sensation to the skin. Another object of the present invention was to provide non-tacky light protection preparations.

It has been found, astonishingly, and therein lies the achievement of all these objects, that water-resistant cosmetic or dermatological light protection formulations in the form of O/W emulsions or hydrodispersions comprising one or more cosmetically or pharmaceutically acceptable hydrophobic inorganic pigments, these pigments being incorporated into the oily phase of the emulsions or hydrodispersions, one or more cosmetically or pharmaceutically acceptable oil-soluble UV filter substances, one or more film-forming agents and furthermore, comprising, if appropriate, one or more cosmetically or pharmaceutically acceptable water-soluble UV filter substances one or more substances chosen from the group consisting of the customary cosmetic or dermatological active compounds, auxiliaries and/or additives in a customary cosmetic or pharmaceutical carrier, remedy the poor state of affairs of the prior art.

Advantageous embodiments of the present invention are, in particular, water-resistant light protection formulations in the form of hydrodispersions which consist of an internal lipid phase and an external aqueous phase and which are essentially free from emulsifiers, comprising one or more cosmetically or pharmaceutically acceptable hydrophobic inorganic pigments, these pigments being incorporated into the oily phase of the hydrodispersions, one or more cosmetically or pharmaceutically acceptable oil-soluble UV filter substances, one or more film-forming agents and furthermore comprising, if appropriate, one or more cosmetically or pharmaceutically acceptable water-soluble UV filter substances one or more substances chosen from the group consisting of customary cosmetic or dermatological active compounds, auxiliaries and/or additives, with the exception of emulsifiers in a customary cosmetic or pharmaceutical carrier.

Another embodiment of the present invention is the use of a composition comprising one or more cosmetically or pharmaceutically acceptable hydrophobic inorganic pigments, one or more cosmetically or pharmaceutically acceptable oil-soluble UV filter substances, one or more film-forming agents for achieving or increasing the water resistance of cosmetic or dermatological light protection formulations which are in the form of O/W emulsions or hydrodispersions, the inorganic pigments being incorporated into the oily phase of the emulsions or hydrodispersions.

It is likewise advantageous if the formulations according to the invention are in the form of O/W emulsions or hydrodispersions.

Light protection formulations based on $TiO_2$ pigments are indeed described in the specifications EP-A 456 458, EP-A 456 459 and EP-A 456 460. Water-resistant systems, in particular emulsifier-free water-resistant systems, however, cannot be realised in such a manner. Pigment-containing hydrodispersions of the type according to the invention also have not yet been disclosed.

It was surprising and not foreseeable that, by following the teaching disclosed here on technical actions, preparations which are entirely satisfactory in any respect are obtainable.

If the formulations according to the invention are in the form of hydrodispersions, it would rather have had to be expected that the pigment microparticles would accumulate to form agglomerates because of the lack of an emulsifier. It was furthermore surprising that the tackiness of the hydrodispersions can be reduced drastically by following the teaching disclosed here on technical actions.

It was furthermore surprising that, and this applies to O/W emulsions as well as to hydrodispersions, by following the teaching disclosed here, water-resistant light protection formulations having outstanding protection properties can be achieved.

Although R. Oteri, St. Johnson and S. Dastis describe some of the film-forming agents which are advantageous according to the invention in "A New Waterproofing Agent for Sunscreen Products", Cosmetics & Toiletries 102, March 1987, pages 107–109, they give no indication that the water resistance which can possibly be achieved in such a manner can be increased further by addition of hydrophobic inorganic pigments.

Finally, it was surprising that the use of inorganic pigments in the formulations according to the invention does not lead to severe dryness of the skin, but in contrast causes a lasting, extremely pleasant sensation on the skin.

It is assumed that the oil-soluble UV filter substances according to the invention are adsorbed onto the surface of the hydrophobic inorganic pigments.

M. Schmidt and S. G. Steinemann indeed report that certain amino acids are easily adsorbed by the surface of titanium dioxide particles in "XPS studies of amino acids adsorbed on titanium dioxide surfaces", Fresenius' Journal of Analytical Chemistry (1991) 341, pages 412–415. However, this work in no way gives an indication of the present invention and its advantageous properties. Furthermore, $TiO_2$, which is mentioned loc. cit., is not hydrophobic.

Cosmetic and dermatological formulations according to the invention preferably comprise inorganic pigments based on metal oxides and/or other metal compounds which are sparingly soluble or insoluble in water, in particular the oxides of titanium ($TiO_2$), zinc (ZnO), iron (for example $Fe_2O_3$), zirconium ($ZrO_2$), silicon ($SiO_2$), manganese (for example MnO), aluminum ($Al_2O_3$) and cerium (for example $Ce_2O_3$), mixed oxides of the corresponding metals and mixtures of such oxides. The pigments are particularly preferably those based on $TiO_2$.

The cosmetic and dermatological acceptability of the substances on which the pigments are based is of course a prerequisite for the usability of inorganic pigments for the purposes according to the invention.

The modifications in which such metal oxides are present are essentially irrelevant to the present invention. For example, $TiO_2$ occurs in nature in three main modifications (rutile, anatase and brookite), which in principle are all equally suitable. The same applies to the modifications of iron oxides and the like.

It is advantageous to choose the particle diameter of the pigments used to be smaller than 100 nm.

According to the invention, the inorganic pigments are present in hydrophobic form, i.e. they have been given a water-repellent treatment on the surface. This surface treatment can comprise providing the pigments with a thin hydrophobic layer by processes known per se.

Such a process comprises, for example, producing the hydrophobic surface layer by a reaction according to n $TiO_2$+m $(RO)_3Si—R'→n$ $TiO_2$ (surf.). n and m here are stoichiometric parameters to be inserted as required, and R and R' are the desired organic radicals. Hydrophobized pigments prepared analogously to DE-A 33 14 742, for example, are of advantage.

Advantageous $TiO_2$ pigments are obtainable, for example, under the tradenames T 805 from DEGUSSA or M 262 from KEMIRA or MT 100 T from TAYCA.

Substances which, after being dissolved in water or organic solvents, are applied to the skin and leave behind a more or less coherent film on the skin after the solvent has evaporated off are regarded as film-forming agents.

Oil-soluble or hydrophobic film-forming agents, such as hydrophobicized polyvinylpyrrolidone derivatives, for example copolymers of polyvinylpyrrolidones with hexadecene or eicosene, are particularly advantageous in the context of the present invention.

The water resistance of formulations comprising water-soluble or hydrophilic film-forming agents can also be increased considerably according to the invention. Film-forming agents which can therefore also advantageously be used according to the invention are those chosen, in particular, from the group consisting of thickeners and gel-forming agents, preferably chosen from the group consisting of polyacrylates, in particular Carbopols, and of these preferably types 980, 981, 1382, 2984 and 5984, in each case individually or in combination, and also polysaccharides and derivatives thereof, for example hyaluronic acid, xanthan gum, hydroxyalkylcellulose, for example hydroxypropylmethylcellulose, and polyvinylpyrrolidones.

Oil-soluble or hydrophobic film-forming agents can be advantageously used together with water-soluble or hydrophilic film-forming agents.

It can be regarded as a particularly astonishing property of the present invention that even relatively readily water-soluble or at least hydrophilic film-forming agents, such as carbomer derivatives or cellulose derivatives, for example hydroxypropylmethylcellulose, can be used according to the invention, and nevertheless a high water resistance of the formulations according to the invention is ensured.

However, with water-insoluble or hydrophobic film-forming agents, a significant increase in water resistance is also to be achieved by applying the teaching according to the invention.

The use of compositions comprising
one or more cosmetically or pharmaceutically acceptable hydrophobic inorganic pigments,
one or more cosmetically or pharmaceutically acceptable oil-soluble UV filter substances,
for achieving or increasing the water resistance of cosmetic or dermatological light protection formulations which are in the form of O/W emulsions or hydrodispersions and comprise one or more oil-soluble or hydrophobic and/or water-soluble or hydrophilic film-forming agents is therefore regarded as a further advantageous embodiment of the present invention.

Water-resistant light protection formulations according to the invention are advantageously characterized by
a content of 0.1 to 15% by weight, in particular 0.5 to 8.0% by weight, of oil-soluble UV filter substances and/or
a content of 0.1 to 10% by weight, in particular 0.5 to 5.0% by weight, of hydrophobic inorganic pigments and/or
a content of 0.1 to 10% by weight, in particular 0.5 to 3.0% by weight, of film-forming agents,
in each case based on the total weight of the composition.

The O/W emulsions or hydrodispersions according to the invention are prepared in accordance with the customary rules, with which the expert is familiar.

It is possible and advantageous to add the hydrophobic inorganic pigment or pigments and the oil-soluble UV filter substance or substances to the emulsion mixture at any desired point in time of the preparation of the emulsion. The pigment or pigments and oil-soluble UV filter substance or substances can be added to the emulsion mixture either separately or already in combination with one another.

It is preferable to incorporate the hydrophobic inorganic pigment and/or the oil-soluble UV filter substance or substances into the oily phase and then to combine the oily phase with the aqueous phase.

It is furthermore preferable if the film-forming agent or agents is or are incorporated into the particular phase for which they have a particular affinity. Water-soluble or hydrophilic film-forming agents are thus preferably added to the aqueous phase and oil-soluble or lipophilic film-forming agents are preferably added to the oily phase.

Particularly advantageous formulations furthermore are obtained if the active compounds according to the invention are combined with antioxidants. According to the invention, the O/W emulsions or hydrodispersions advantageously comprise one or more antioxidants. All the antioxidants which are suitable or customary for cosmetic and/or dermatological uses are used as antioxidants which are favourable but nevertheless to be used optionally.

The antioxidants are particularly advantageously chosen from the group consisting of ascorbic acid (vitamin C), ascorbic acid derivatives, the various tocopherols (vitamin E) and tocopheryl esters or other tocopherol derivatives, folic acid (previously called vitamin $B_c$, $B_9$ or M, now assigned to the vitamin $B_2$ group), phytic acid (inositolhexaphosphoric acid, also fytic acid), the various ubiquinones (mitoquinones, coenzyme Q), bile extract, cis- and/or trans-urocanic acid (4-imidazolylacrylic acid), carnosine (N-β-alanyl-L-histidine, ignotine), histidine, flavones or flavonoids, cystins (3,3'-dithiobis(2-aminopropionic acid)), cystsine (2-amino-3-mercaptopropionic acid) and derivatives thereof (for example N-acetylcysteine), the various carotenes (in particular β-carotene and lycopene (psi-carotene)), tyrosine (2-amino-3-(4-hydroxyphenyl)-propionic acid), α-liponic acid (1,2-dithiolane-3-pentanoic acid), glutathione (gamma-L-glutamyl-L-cysteineglycine) and glutathione esters, furalglucitol (sorbitylfurfural), mannitol and zinc oxide and zinc salts (for example $ZnSO_4$). It had not been possible to predict that the combinations according to the invention with antioxidants lead to products which are tolerated by the skin or increase the tolerability thereof and do not affect the endogenous skin microflora on healthy skin.

The oil-soluble UV filter substances according to the invention can advantageously be chosen from the group consisting of substances which absorb UV radiation chiefly in the UVB range, the total amount of filter substances being, for example, 0.1% by weight to 15% by weight, preferably 0.5 to 10% by weight, in particular 0.5 to 8.0% by weight, based on the total weight of the formulation.

Advantageous oil-soluble UVB filters are, for example:

3-benzylidenecamphor derivatives, preferably 3-(4-methylbenzylidene) camphor and 3-benzylidenecamphor;

4-aminobenzoic acid derivatives, preferably 2-ethylhexyl 4-(dimethylamino)-benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxybenzalmalonate; and 2,4,6-trianilino-(p-carbo-2'-ethyl-1'-hexyloxy)-1,3,5-triazine.

Where appropriate, it is also advantageous additionally to incorporate water-soluble UV filter substances into the formulations according to the invention. Advantageous water-soluble UVB filters are, for example:

salts of 2-phenylbenzimidazole-5-sulphonic acid, such as its sodium, potassium or its triethanol-ammonium salt, and the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl) sulphonic acid and its salts.

The oil-soluble UV filter substances according to the invention are especially advantageously chosen from the group consisting of oil-soluble substances which absorb UV radiation chiefly in the UVA range. Oil-soluble UVA filters which can advantageously be used according to the invention are, for example, derivatives of dibenzoylmethane, in particular 1-(4'-tert-butylphenyl)-3-(4'-methoxyphenyl) propane-1,3-dione and 1-phenyl-3-(4'-isopropylphenyl) propane-1,3-dione.

The total amount of DVA filter substances can advantageously be 0.1% by weight to 15% by weight, preferably 0.5 to 10% by weight, in particular 0.5 to 8.0% by weight, based on the total weight of the formulation.

Emulsions according to the invention, for example in the form of a sunscreen cream or a sunscreen milk, are advantageous and comprise, for example, the fats, oils, waxes and other fatty substances mentioned, as well as water and an emulsifier such as is usually used for such a type of formulation.

Those cosmetic and dermatological formulations which are in the form of a sunscreen composition, a pré-soleil soleil or après-soleil product, are advantageous according to the invention. These advantageously additionally comprise at least one UVA filter substance and/or at least one UVB filter substance.

Those cosmetic and dermatological formulations which are in the form of a sunscreen composition, a pré-soleil or après-soleil product, and comprise one or more antioxidants in addition to the UVA filter or filters and/or the UVB filter or filters are furthermore particularly advantageous according to the invention.

The total amount of antioxidants can advantageously be 0.1% by weight to 30% by weight, preferably 0.5 to 10% by weight, in particular 1 to 6% by weight, based on the total weight of the formulation.

If desired, the cosmetic formulations according to the invention can furthermore comprise cosmetic auxiliaries such as are usually used in such formulations, for example preservatives, bactericides, substances having a deodorizing action, antiperspirants, insect repellents, vitamins, agents for preventing foaming, dyestuffs, pigments having a colouring action, thickening agents, softening substances, moisturizing and/or moisture-retaining substances, fats, oils, waxes or other customary constituents of a cosmetic formulation, such as alcohols, polyols, polymers, foam stabilizers, electrolytes, organic solvents or silicone derivatives.

Finally, amino acids can be chosen as active compounds or additives having particularly advantageous properties, and these are preferably from the group consisting of glycine, alanins, valine, leucine, isoleucine, phenylalanine, tyrosine, proline, hydroxyproline, serine, threonine, cystsine, methionine, trlrptophan and arginine. Of these amino acids, arginine is particularly preferred and glycine is especially preferred.

Advantageous embodiments of the present invention are described in the following Examples.

|  | % by weight |
|---|---|
| Example 1 Sun cream, O/W, light protection factor 20 | |
| Cyclomethicone | 3.00 |
| Glyceryl stearate + PEG 30 stearate | 2.00 |
| Wool wax alcohol | 0.10 |
| Glyceryl stearate | 3.00 |
| Isopropyl palmitate | 2.00 |
| Octyldodecanol | 1.00 |
| $C_{12-15}$-alkyl benzoate | 2.00 |
| Glycerol | 3.00 |
| Cetyl alcohol | 3.00 |
| Myristyl myristate | 2.00 |
| Phenylbenzimidazolesulphonic acid | 3.00 |

|  | % by weight |
|---|---|
| Tocopheryl acetate | 0.50 |
| EDTA solution (20% strength) | 0.50 |
| NaOH (45% strength) | 1.15 |
| Ethyl alcohol | 4.00 |
| Preservative | q.s. |
| Perfume | q.s. |
| Hydrophobic TiO₂, particle size <100 nm | 2.00 |
| PVP/eicosene copolymer | 3.00 |
| Octyl methoxycinnamate | 4.50 |
| Butylmethoxydibenzoylmethane | 2.00 |
| Water, completely desalinated | to 100.00 |

Example 2
Sun cream, O/W, light protection factor 8

|  | % by weight |
|---|---|
| Cyclomethicone | 3.00 |
| Glyceryl stearate + PEG 30 stearate | 2.00 |
| Glyceryl stearate | 3.00 |
| Isopropyl palmitate | 2.00 |
| Octyldodecanol | 3.00 |
| Glycerol | 3.00 |
| Cetyl alcohol | 3.00 |
| Tocopheryl acetate | 0.50 |
| EDTA solution (20% strength) | 0.50 |
| NaOH | q.s. |
| Ethyl alcohol | 1.50 |
| Preservative | q.s. |
| Perfume | q.s. |
| Hydrophobic TiO₂, particle size <100 nm | 1.00 |
| Octyl methoxycinnamate | 5.00 |
| Butylmethoxydibenzoylmethane | 0.50 |
| PVP/hexadecene copolymer | 1.50 |
| Water, completely desalinated | to 100.00 |

Example 3
Sun milk, O/W

|  | % by weight |
|---|---|
| Trilaureth-4 phosphate | 0.75 |
| Triceteareth-4 phosphate | 1.00 |
| Glyceryl stearate + PEG 100 stearate | 1.00 |
| Glyceryl stearate + ceteareth-20 | 0.80 |
| Glyceryl lanolate | 0.50 |
| Isopropyl palmitate | 3.00 |
| Glycerol caprylate/caproate ("Caprylic/capric triglyceride") | 5.00 |
| Cetyl alcohol | 1.00 |
| Phenylbenzimidazolesulphonic acid | 4.00 |
| Butylated hydroxytoluene | 0.06 |
| EDTA solution (20% strength) | 0.50 |
| NaOH | q.s. |
| Preservative | q.s. |
| Hydrophobic TiO₂, particle size <100 nm | 3.00 |
| Octyl methoxycinnamate | 6.00 |
| Butylmethoxydibenzoylmethane | 0.50 |
| Methylbenzylidenecamphor | 3.00 |
| PVP/eicosene copolymer | 1.00 |
| Water, completely desalinated | to 100.00 |

Example 4
Sun milk, O/W

|  | % by weight |
|---|---|
| Cyclomethicone | 2.00 |
| Cetearyl alcohol + PEG 40 hydrogenated castor oil + sodium cetearyl sulphate | 2.50 |
| Glyceryl lanolate | 1.00 |
| Glycerol caprylate/caproate ("caprylic/capric triglyceride") | 2.00 |
| Octyl stearate | 3.00 |
| Castor oil | 4.00 |
| Glycerol | 3.00 |
| Butylated hydroxytoluene | 0.03 |
| EDTA solution (20% strength) | 0.50 |
| NaOH | q.s. |
| Preservative | q.s. |
| Perfume | q.s. |
| Hydrophobic TiO₂, particle size <100 nm | 1.50 |
| Carbomer 981 | 0.23 |
| Octyl methoxycinnamate | 4.00 |
| Butylmethoxydibenzoylmethane | 2.00 |
| Methylbenzylidenecamphor | 3.50 |
| Hydroxypropylmethylcellulose | 0.30 |
| PVP/hexadecene copolymer | 1.50 |
| Water, completely desalinated | to 100.00 |

Example 5
Sun milk, O/W

|  | % by weight |
|---|---|
| Stearic acid | 2.00 |
| Cetyl palmitate | 1.00 |
| Glycerol caprylate/caproate ("caprylic/capric triglyceride") | 2.00 |
| Sorbitan monooleate | 1.00 |
| Sorbitan monostearate | 1.50 |
| Paraffin oil, DAB 9 | 1.29 |
| Cetearyl alcohol | 0.80 |
| Glycerol | 3.00 |
| Butylated hydroxytoluene | 0.06 |
| Simethicone | 0.20 |
| Polyethylene glycol 150 | 3.00 |
| Triethanolamine | 0.85 |
| Ethyl alcohol | 3.00 |
| Preservative | q.s. |
| Perfume | q.s. |
| Hydrophobic TiO₂, particle size <100 nm | 2.00 |
| Octyl methoxycinnamate | 5.00 |
| Methylbenzylidenecamphor | 1.00 |
| Carbomer 981 | 0.10 |
| PVP/hexadecene copolymer | 2.00 |
| Water, completely desalinated | to 100.00 |

Example 6
sun hydrodispersion gel, light protection factor 12

|  | % by weight |
|---|---|
| Phenyltrimethicone | 4.50 |
| Ethanol | 9.00 |
| Glycerol | 4.50 |
| EDTA solution (14% strength) | 0.75 |
| Trisaminopromethamine | 2.01 |
| Perfume, preservative, dyestuffs | q.s. |
| Hydrophobic TiO₂, particle size <100 nm | 4.50 |
| Octyl methoxycinnamate | 7.50 |
| Parsol ® 1789 | 3.00 |
| Hydroxypropylmethylcellulose | 0.30 |
| Carbomer 981 | 1.50 |
| PVP/hexadecene copolymer | 1.00 |
| Water, completely desalinated | to 100.00 |

Example 7
Sun hydrodispersion gel, light protection factor 12

|  | % by weight |
|---|---|
| Octyldodecanol | 4.50 |
| Ethanol | 9.00 |
| Butylene glycol | 4.50 |
| EDTA solution (14% strength) | 0.75 |
| Trisaminopromethamine | 2.01 |
| Perfume, preservative, dyestuffs | q.s. |
| Hydrophobic TiO₂, particle size <100 nm | 4.50 |
| Octylmethoxycinnamate | 7.50 |
| Parsol ® 1789 | 3.00 |
| Carbomer 981 | 1.50 |
| Hydroxypropylmethylcellulose | 0.30 |
| PVP/eicosene copolymer | 1.50 |
| Water, completely desalinated | to 100.00 |

Example 8
Sun hydrodispersion gel, light protection factor 12

|  | % by weight |
|---|---|
| Castor oil | 4.50 |
| Ethanol | 9.00 |
| Butylene glycol | 4.50 |
| EDTA solution (14% strength) | 0.75 |
| Trisaminopromethamine | 2.01 |
| Perfume, preservative, dyestuffs | q.s. |
| Hydrophobic TiO₂, particle size <100 nm | 4.50 |
| Octyl methoxycinnamate | 7.50 |
| Parsol ® 1789 | 3.00 |
| Carbomer 981 | 1.50 |
| Hydroxypropylmethylcellulose | 0.30 |
| Water, completely desalinated | to 100.00 |

We claim:

1. A water-resistant cosmetic or dermatological light protection formulation in the form of an O/W emulsion or a hydrodispersion, comprising one or more cosmetically or pharmaceutically acceptable silanized hydrophobic inorganic pigments, said pigments being incorporated into the oily phase of the emulsions or hydrodispersions, one or more cosmetically or pharmaceutically acceptable oil-soluble UV filter substances, one or more film-forming agents and furthermore, optionally comprising, one or more cosmetically or pharmaceutically acceptable water-soluble UV filter substances one or more substances selected from the group consisting of a customary cosmetic or dermatological active compound, an auxiliary or an additive in a customary cosmetic or pharmaceutical carrier.

2. A water-resistant light protection formulation in the form of a hydrodispersion which consists of an internal lipid phase and an external aqueous phase and which is essentially free from emulsifiers, comprising one or more cosmetically or pharmaceutically acceptable silanized hydrophobic inorganic pigments, said pigments being incorporated into the oily phase of the hydrodispersions, one or more cosmetically or pharmaceutically acceptable oil-soluble UV filter substances, one or more film-forming agents and furthermore optionally comprising, one or more cosmetically or pharmaceutically acceptable water-soluble UV filter substances, one or more substances selected from the group consisting of a customary cosmetic or dermatological active compound, an auxiliary or additive, with the exception of emulsifiers in a customary cosmetic or pharmaceutical carrier.

3. A water-resistant cosmetic or dermatological formulation according to claim 1, wherein the oil-soluble UV filter substance is selected from the group consisting of a 3-benzylidenecamphor derivative;

a 4-aminobenzoic acid derivative;

an ester of cinnamic acid;

an ester of salicylic acid;

a derivative of benzophenone;

an ester of benzalmalonic acid; or 2,4,6-trianiline-(p-carbo-2'-ethyl-1'-hexyloxy)-1,3,5-triazine.

4. A formulation according to claim 1, wherein to film-forming agent is hydrophilic.

5. A formulation according to claim 1, wherein to film-forming agent is cellulosic.

6. A formulation according to claim 1, wherein to film-forming agent is hydrophobic.

7. A formulation according to claim 1, wherein to film-forming agent is polyvinylpyrrilidone.

8. A method of forming a light-protective film on skin which comprises applying thereto hydrodispersion according to claim 1.

9. A method of forming a light-protective film on skin which comprises applying thereto hydrodispersion according to claim 1.

10. A method of forming a light-protective film on skin which comprises applying thereto an o/w emulsion or hydrodispersibn according to claim 2.

11. A method of forming a light-protective film on skin which comprises applying thereto an o/w emulsion or hydrodispersion according to claim 4.

12. A method of forming a light-protective film on skin which comprises applying thereto an o/w emulsion or hydrodispersion according to claim 5.

13. A method of forming a light protective film on skin which comprises applying thereto an o/w emulsion or hydrodispersion according to claim 6.

14. A method of forming a light-protective film on skin which comprises applying thereto an o/w emulsion or hydrodispersion according to claim 7.

* * * * *